United States Patent [19]
Klicek et al.

[11] Patent Number: 5,372,596
[45] Date of Patent: Dec. 13, 1994

[54] APPARATUS FOR LEAKAGE CONTROL AND METHOD FOR ITS USE

[75] Inventors: Michael S. Klicek, Boulder; William G. Paterson, Longmont, both of Colo.

[73] Assignee: Valleylab Inc., Boulder, Colo.

[21] Appl. No.: 97,737

[22] Filed: Jul. 27, 1993

[51] Int. Cl.⁵ .......................................... A61B 17/39
[52] U.S. Cl. ................................ 606/35; 606/38; 606/34
[58] Field of Search ............................ 606/32–35, 606/37–40

[56] References Cited

U.S. PATENT DOCUMENTS

| | | | |
|---|---|---|---|
| 4,102,341 | 7/1978 | Ikuno et al. | 606/35 |
| 4,200,105 | 4/1980 | Gonser | 606/35 |
| 4,658,819 | 4/1987 | Harris et al. | 606/34 |
| 5,152,762 | 10/1992 | McElhenney | 606/35 |
| 5,167,658 | 12/1992 | Ensslin | 606/34 |

Primary Examiner—Stephen C. Pellegrino
Assistant Examiner—Michael Peffley
Attorney, Agent, or Firm—Peter C. Richardson; Lawrence C. Akers; Aaron Passman

[57] ABSTRACT

Apparatus and method find leakage due to tissue load or transients and has active and return electrodes for RF energy sensed by transformers for a circuit that finds leakage at more than two thousand times per second or a frequency dependent on the phase shift between voltage and current. Software and feedback manage $V_{rms}$ to reduce the voltage or increase the crest factor, which is $V_{rms}$ divided by peak voltage, by pulse width modulation of the RF drive. Voltage and current phase shift changes, angle $\theta$, are compared to a threshold, and when greater, the frequency at which the differences between the active and return current signals are examined is increased. The differences between the active and return currents are examined and when greater than maximum leakage while in coagulation mode, the RF drive pulse width is reduced to maintain voltage wave peaks at a preset value and reduce $V_{rms}$ thereby reducing leakage to the allowable maximum. Reducing the duty cycle or the pulse width of the output wave increases the crest factor. When the differences between active and return currents are greater than a maximum for leakage while in cut or bipolar mode, the $V_{rms}$ is reduced to limit leakage to a maximum level. When the phase angle $\theta$ is less than a threshold, the frequency with which leakage is examined is reduced.

25 Claims, 2 Drawing Sheets

APPARATUS FOR LEAKAGE CONTROL AND METHOD FOR ITS USE

FIELD OF INVENTION

This invention pertains to the field of electrosurgery and more particularly, to controlling an electrosurgical generator unit (ESU) by algorithms for specific output modes to reduce leakage currents, particularly during the transition between open circuit and contact with tissue and back to open circuit.

BACKGROUND OF THE DISCLOSURE

Electrosurgery is the application of a radio frequency electrical energy to a surgical site on a human or animal for tissue cutting, coagulation, or a blend thereof. In monopolar mode the radio frequency current that is generated by an ESU is applied to tissue from an active electrode held by the surgeon, and is collected from a dispersive electrode attached to the patient. A small contact area of the active electrode causes a high current density so that a spark enters the tissue at the surgical site. This spark causes intense localized heating, eschar, fulguration and other effects, to achieve the cutting and/or coagulation. The dispersive electrode collects the energy returning it to the ESU to complete an electrical circuit. The dispersive electrode is of a significant size so that the energy density collected thereby is low enough to avoid any surgical or heating effect that would burn.

A burn will develop if the power delivered to the tissue and after its passage through the body results in a high energy density at the exit so that localized tissue heating occurs. This situation happens when the energy is allowed to leave a patient's body at a location other than the dispersive electrode. Such a condition is called leakage. A burn from leakage can be quite severe as the patient is anesthetized and will not react thereto. The burn area is frequently covered so the doctor or surgical attendants will not see it until it is too late to take corrective action.

Another potential path for leakage burns is to the surgeon through contact with the active electrode or the conductors which supply the radio frequency, high voltage electrosurgical energy. Leakage in that circumstance may harm or burn the surgeon or one of the surgical attendants in contact with the active electrode or its supply conductor and a ground. It is for this reason that leakage or alternate path energy flow in electrosurgery are of considerable concern and efforts are made to monitor and control leakage.

The early electrosurgical units (ESU) were of a ground referenced design. Being ground referenced, the return for the ESU and the dispersive electrode were both connected to earth or ground. The ground referenced arrangement was satisfactory provided that no other point on the patient was grounded. When a monitoring electrode, i.e. EKG, was used during the electrosurgical procedure, and the monitoring electrode was referenced to ground, some portion of the electrosurgical energy could flow to ground through the monitoring electrode, instead of the preferred path back through the dispersive electrode. Since monitoring electrodes usually have small contact area, the current density at their contact may be sufficient to develop enough energy density to result in a burn. An even worse condition occurs if the electrosurgical generator connection to the dispersive electrode is accidentally separated. Thus, with no direct energy path back to the ESU, all of the power travels through any alternate grounded paths, such as through the monitoring electrodes, the surgeon and/or the surgical table. Severe burns are a possible result.

In an effort to reduce the risks associated with the ground referenced ESUs, the power output circuit of the ESU was isolated from any other ground. Output isolated ESUs were a significant step in reducing the risks associated with alternate path burns, because the electrosurgical energy exiting the patient was more likely to flow through the dispersive electrode to complete the circuit and not through any other ground referenced points when returning to the ESU. If the generator connection to the dispersive electrode became disconnected, a significant portion of the electrosurgical energy flow from the ESU would stop.

Although isolated output ESUs was an improvement over the previous ground referenced units, a problem remained because the isolation from ground was not always perfect. At the relatively high frequencies of electrosurgical current, e.g., 500 kilohertz to 1 megahertz, stray capacitance to ground allows another ground referenced path. Furthermore, the amount of stray capacitance required to create this other significant path for ground referenced energy flow is not great. Although alternate paths of energy flow are less than those flowing if the ESU was ground referenced, a potential exists for significant patient and alternate path burns.

An improvement to help minimize alternate paths for energy in isolated electrosurgical generators includes the use of a differential transformer in the output circuit, as shown in U.S. Pat. No. 4,437,464. The electrosurgical energy supplied to the active electrode flows through a winding on a transformer core, and the energy from the dispersive electrode flows through a winding wound opposite to the direction of the winding for the active energy flow on that core. Normally the energy passing through the two windings are equal and of opposite direction, as would be the case when there is no alternate path. Thus, the counteracting fluxes therefrom cancel each other. The transformer core presents very little loss or impedance to the flow of electrosurgical energy.

If a significant alternate path exists, the imbalance created thereby results in a flux in the core of the differential transformer causing a measurable loss that increases the impedance and reduces the amount of energy flowing to the active electrode. Thus, the current flow through the active electrode to the patient is automatically inhibited and therefore reduced, thereby causing a commensurate decrease in the alternate path leakage flow. Although this approach reduces leakage, it may not be sufficient to reduce the leakage below a maximum acceptable safe energy level, for example one hundred fifty milliamps.

Another improvement, which provides an alarm or terminates the delivery of electrosurgical power under conditions of excessive leakage with an isolated ESU, is disclosed in U.S. Pat. No. 3,683,923. A third or sensing winding on the differential transformer responds to the imbalance in the flow of energy through the active winding and the return winding. The third winding, upon sensing a sufficient imbalance between the energy flow, triggers an alarm circuit for the operator. A relay may simultaneously or alternatively be activated to terminate the flow of energy to the tissue. The operator may take corrective action such as reducing the power level or attempting to eliminate the problem causing leakage, as well as reactivating the ESU.

U.S. Pat. No. 4,094,320, assigned to the owner of the present invention, has a compensating means for varying the threshold at which the leakage current detected will control the output signal of the generator. The sensitivity of the threshold is thereby regulated. U.S. Pat. No. 4,188,927, assigned to the assignee as the present invention, has a leakage threshold varied in accord with the mode selected so that power output is lower with the desiccation mode than with a mode that permits arcing. A further approach is the use of the signal from the third winding as input for an automatic feedback loop that controls the energy output from the electrosurgical generator to the patient. Such control responds to the leakage measured, as a function of the difference between active and return energy flow, by reducing the output smoothly. U.S. Pat. No. 5,152,762 discloses such a circuit designed to apply the past technology for sensing the leakage to circuitry including a feedback control having a loop to regulate the ESU output. Imbalance is sensed in an isolation transformer winding responsive to the difference in energy flow between the active and return electrodes. The signal generated is considered with an accepted maximum amount and then the requested output to insure that the ESU output is regulated. U.S. Pat. No. 4,658,819, assigned to the assignee of the invention herein, has a circuit that decreases the output power in accord with the square of the increase of the impedance.

The problem of the transient conditions including varying loadings or sparks or arcing during the initiation or termination of the electrosurgical effects remains. Specifically, situations wherein the active electrode is not in electrical contact with the patient's tissue such that the energy transmitted to the tip of the electrode must be sufficient to complete the open circuit without causing leakage. Those transient conditions require accelerated handling of the imbalance measured in the transformer. The leakage circuitry must be able to not only take into account the activated mode of the generator but also change the sampling rate of the signal as the leakage becomes more critical.

Against this background and with an appreciation of the problem of transient conditions, further significant improvements and advancements in the control of leakage currents, particularly during initiation and termination, to account for open circuit conditions, are required. Described herein are an instantaneous leakage control and a method of its use that is not found in the literature or practiced in the field. The literature is of interest for its teachings of the knowledge of skilled artisans at the time of this invention of a leakage control and a method use thereof.

SUMMARY OF THE INVENTION

An apparatus for controlling leakage in a radio frequency electrosurgical system during changes in the load as a function of tissue being electrosurgically treated or transient conditions such as the initiation or termination of an electrosurgical effect. An active electrode, not in electrical contact with the patient's tissue, transmits energy from a tip thereof. The apparatus may include an electrosurgical unit for providing radio frequency energy at an active output thereof and for controlling the flow of the energy through the active output. The electrosurgical unit may have a return input. An electrode is preferably connected to the active output for transmitting electrosurgical radio frequency energy to a patient in an electrosurgical procedure such as cutting, coagulating or a blending thereof.

A return electrode may be connected to the patient for receiving radio frequency energy supplied to the patient during the electrosurgical procedure and returning it to the return input of the electrosurgical unit. An inductive transformer responsive to the active output provides a signal of active energy flow. An inductive transformer responsive to the return input provides a signal of return energy flow. A comparison circuit is most preferably connected to receive the active and return signals as a measure of leakage and for determining instantaneous differences at rates greater than two thousand times per second or at a speed sufficient to handle transients. The comparison circuit may examine the differences at a frequency dependent on the phase shift between the output voltage and current of the electrosurgical unit. Leakage of 150 ma is typically the cut off point in an electrosurgical generator safety circuit here, however, the phase difference, leakage about 150 ma or rate of change of leakage current affects the rate of leakage monitoring.

The electrosurgical unit most preferably may include a microprocessor having software programmed with one or more algorithms for determining the differences between the active and return current signals and for examining the differences at a frequency dependent on the phase shift between the output voltage and current of the electrosurgical unit. The comparison circuit in the preferred embodiment has a closed loop feedback for monitoring and controlling the output RMS voltage by reducing the peak voltage of the output wave shaped therefrom or by increasing the crest factor. The crest factor may be increased by pulse width modulation of the radio frequency drive.

The algorithm may be used for determining the differences between the active and return current signals and for examining the differences ascertains the phase shift between the radio frequency voltage and current at the peaks thereof respectively. The algorithm is preferably the Cosine of the phase angle $\theta$ is $((V_{max})^2 + (I_{max})^2 - (V\text{-}I)_{max}^2)_{max}$ divided by $2\ V_{max}\ I_{max}$. The phase angle $\theta$ is compared to a threshold reference. If the phase angle $\theta$ is greater than the reference threshold, the frequency at which the differences between the active and return current signals are examined is increased accordingly. The differences between the active and return current signals may be examined in the comparison circuit and if greater than a maximum for leakage while the mode selected is coagulation then the pulse width of the radio frequency drive is reduced to maintain voltage wave-form peaks at a predetermined value while the RMS voltage is reduced to lower the leakage to a maximum allowed level.

The differences between the active and return current signals might also be examined in the comparison circuit and if greater than a maximum for leakage while the mode selected is coagulation then the frequency at which the leakage current is calculated in the comparison circuit so a maximum allowed level is maintained until the phase angle $\theta$ is smaller than the threshold. The crest factor is increased by reducing the duty cycle or the pulse width of the output wave shape. The differences between the active and return current signals may alternatively be examined in the comparison circuit and if greater than a maximum for leakage while the mode selected is cut or bipolar then the $V_{rms}$ is reduced by lowering the electrosurgical unit radio frequency stage voltage until the differences lower the leakage to a maximum allowed level.

The differences between the active and return current signals could alternately be examined in the comparison circuit and if greater than a maximum for leakage while the mode selected is cut or bipolar then the frequency at which the leakage current is calculated in the comparison circuit so the maximum allowed level of leakage current remains high until the phase angle $\theta$ is smaller than the threshold.

A method for controlling leakage in a radio frequency electrosurgical system during operation under varying tissue loads or through at least transient or open circuit conditions during the initiation or termination of an electrosurgical effect wherein an active electrode in or not in electrical contact with the patient's tissue transmits energy to a tip thereof may include the step of providing an electrosurgical unit having radio frequency energy at an active output thereof. The added step of controlling the flow of the energy through the active output with the electrosurgical unit may follow. Then the step of having a return input connected to the electrosurgical unit may be used. Thereafter the steps of connecting an electrode to the active output and transmitting electrosurgical radio frequency energy to a patient in an electrosurgical procedure such as cutting, coagulating or a blending thereof might be employed. The further steps of connecting a return electrode to the patient and receiving radio frequency energy supplied to the patient during the electrosurgical procedure are preferred. The additional step of returning all but a preset maximum amount of radio frequency energy supplied to the return input of the electrosurgical unit is followed. Then the steps of providing an inductive transformer responsive to the active output for supplying a signal of active energy flow and providing an inductive transformer responsive to the return input for supplying a signal of return energy flow are measured. Next may be the step of using a comparison circuit connected to receive the active and return signals to measure leakage and determine instantaneous differences at a rate of at least two thousand times per second is desired. Finally the step of examining the instantaneous differences at a frequency increase in accord with the phase shift between the output signals of voltage and current is preferred.

The method may have the added step of including a microprocessor having software programmed with one or more algorithms for calculating the differences between the active and return current signals and for examining the differences at a frequency dependent on the phase shift between the output energy of the electrosurgical unit. An additional step might include monitoring and controlling the output RMS voltage by reducing the peak voltage of the output wave shaped therefrom or by increasing the crest factor with a closed loop feedback.

The added method step of increasing the crest factor by pulse width modulation of the radio frequency drive may be used. The added step of using the algorithms for calculating the differences between the active and return current signals and for examining the differences to ascertain the phase shift between the radio frequency voltage and current at the maximums thereof respectively may be selected. The added step of using the particular algorithm for calculating the Cosine of the phase angle $\theta$ is $((V_{max})^2+(I_{max})^2-(V-I)_{max}^2)$ divided by $2\ V_{max}\ I_{max}$ may in the preferred embodiment be included. The added step of comparing the phase angle $\theta$ to a threshold and if it is greater then the threshold, the frequency at which the differences between the active and return current signals are examined, is increased accordingly is in the most preferred method employed.

The added step of examining the differences between the active and return current signals in the comparison circuit and if greater than the preset maximum of radio frequency energy supplied to the return input or leakage while the mode selected is coagulation then reducing the pulse width of the radio frequency drive to maintain voltage wave form peaks at a predetermined value as the RMS voltage is reduced to lower the leakage to the maximum allowed level is a preferred possibility. The additional or alternate step of examining the differences between the active and return current signals in the comparison circuit and if greater than the preset maximum amount of radio frequency energy supplied to the return input or leakage while the mode selected is coagulation then the frequency at which the leakage current is calculated in the comparison circuit so a maximum allowed level is maintained until the phase angle $\theta$ is smaller than the threshold is possible. The added step of examining the differences between the active and return current signals are in the comparison circuit and if greater than the preset maximum amount of radio frequency energy supplied to the return input or leakage while the mode selected is cut or bipolar then reducing the $V_{rms}$ by lowering the electrosurgical unit radio frequency stage voltage until the differences produce the leakage lowered to the maximum allowed level is a further method.

The required microprocessor samples output voltage and current waveforms approximately 8 million times per second. Digital signal processing then performs calculations with this sampled output voltage and current waveform data to control the output of the electrosurgical generator based on the results of these calculations. The microprocessor is able to complete the full complement of calculations for adjusting the generator output approximately 1000 times per second. Because the number of calculations is great, the control rate achieved is about 300 times per second. To improve this, a scheme in which unneeded calculations are limited, thus increasing the control feedback loop rate for remaining calculations. This is accomplished by determining if indications of significant RF leakage currents exist by measuring phase difference between output voltage and current. If the difference in phase is small, the calculations associated with leakage current are minimized, i.e., performed once every 64 or 128 loops. This is effective because the control system operates faster when the output of the generator is loaded by contact with tissue (and the leakage current was minimal), and slower when the output is not loaded and the main control parameter is leakage current.

The added step of examining the differences between the active and return current signals in the comparison circuit and if greater than the preset maximum amount of radio frequency energy supplied to the return input or leakage while the mode selected is cut or bipolar then maintaining the frequency at which the leakage current is calculated in the comparison circuit so the preset maximum amount of radio frequency energy supplied to the return input or leakage or allowed level is high until the phase angle $\theta$ is smaller than the threshold may offer an extra approach. The added step of increasing the crest factor by reducing the duty cycle or the pulse width of the output wave shape is then possible.

DETAILED DESCRIPTION OF THE INVENTION

The claims are not limited to the circuit for leakage control described and illustrated by way of example and the methods of use specifically explained. The claims are to be considered in view of the existing knowledge of skilled artisans in the Field prior to the inventions defined by the language of the claims herein as amended or considered in view of knowledge of skilled artisans prior to these inventions.

Figure 1:
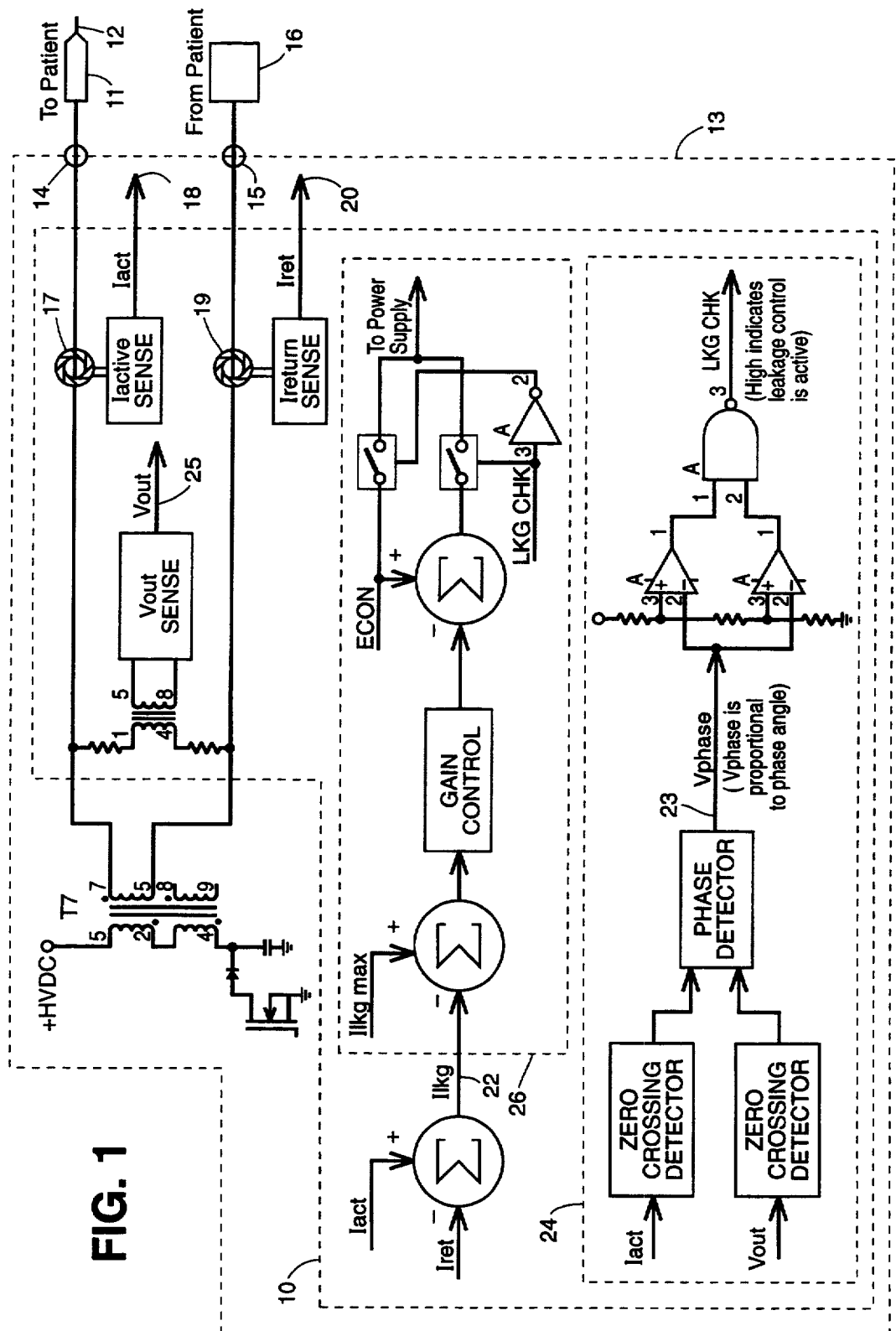
FIG. 1 is a schematic block diagram showing the comparison circuit used with an electrosurgical generator to calculate phase shift and control the rate at which the leakage is measured and corrected.

In FIG. 1 there is a schematic block diagram of an apparatus for controlling leakage 10 in a radio frequency electrosurgical system which senses changes in the load as a function of tissue being electrosurgically treated or transient conditions such as the initiation or termination of an electrosurgical effect even when an active electrode 11 is not in electrical contact with the patient's tissue and transmits energy to a tip 12 thereof. The active electrode 11 connects to an electrosurgical unit 13 such as the Force 40 generator manufactured by Valleylab Inc. of Boulder, Colo. for providing radio frequency energy at an active output thereof and for controlling the flow of the energy through the active output 14, the electrosurgical unit 13 also has a return input 15. The active electrode 11 connects to the active output 14 for transmitting electrosurgical radio frequency energy to a patient during any electrosurgical procedure such as cutting, coagulating or a blending thereof. The system can be monopolar or bipolar depending on the electrode configuration.

A return electrode 16 connects to the patient for receiving radio frequency energy supplied to the patient during any electrosurgical procedure and returns the energy to the return input 15 of the electrosurgical unit 13. An inductive transformer 17, made by Pulse Engineering of San Jose, Calif., senses energy flow about the active output 14 and is responsive to the active output 14 providing a signal 18 in the form of a direct current voltage of active energy flow. Another inductive transformer 19 senses energy flow about the return input 15 and is responsive to the return input 15 providing a signal 20 in the form of a direct current voltage of return energy flow.

A comparison circuit 21, such as AD 827 by Analog Devices of Norwood, Mass., connects to receive the active and return signals 18 and 20 as a measure of leakage and for determining instantaneous differences 22 in those signals 18 and 20 at rates sufficient to handle transients. The comparison circuit 21 examines and instantaneously measures to thereafter calculate differences 22 at a variable frequency dependant on the phase shift 23 between the proportional output voltage 25 and proportional current 18 of the electrosurgical unit 13. The phase shift 23 is a function of the laws of nature and is a measure of inductive or capacitive load across the active and return electrodes 12 and 16 during operation. Purely resistive loads do not shift phase and are not measured or used to change the frequency at which the leakage is measured.

The electrosurgical unit 13 may include microprocessor 24, such as AD 2105 manufactured by Analog Devices of Norwood, Mass., having software programmed with one or more algorithms for instantaneously determining the leakage from differences between the active and return current signals 18 and 20 and for examining those differences at varying frequencies dependent on the phase shift 23 between the output proportional voltage 25 and proportional current 18 of the electrosurgical unit 13. The details inside the dashed line indicating phase shift comparison portion of the microprocessor 24 which includes a closed loop feedback 26 is included for understanding by way of example. The closed loop feedback 26 monitors and controls the proportional output 25 RMS voltage by reducing the peak voltage of the output wave shape therefrom or by increasing the crest factor. The crest factor is increased by pulse width modulation of a group of pulses of the radio frequency drive. Microprocessor 24 has a phase comparison circuit.

The algorithm used for determining the leakage due to measured differences 22 between the active and return current signals 18 and 20 and for examining frequently those differences 22 and the phase shift 23 between the proportional radio frequency voltage 25 and proportional current 18 at the peaks thereof, respectively a voltage, $V_{phase}$ 23 that is compared to a threshold and if greater, then the leakage checking signal is sent to the microprocessor 24. The algorithm in the preferred embodiment of the software is:

Cosine of the phase angle $\theta = ((V_{max})^2 + (I_{max})^2 - (V-I)_{max}^2)$ divided by $2 V_{max} I_{max}$. As in FIG. 1, the phase comparison is performed in circuit 27. The phase angle $\theta$ is compared to a threshold and if the phase angle $\theta$ is greater, then the frequency at which the differences 22 between the active and return current signals 18 and 20 are examined is increased accordingly. The Cosine of the phase angle is $(V_{max})^2 + (I_{max})^2 - (V-I)^2 / 2(V_{max} * I_{max})$ and this would be an alternative to measuring the V output to I output phase relationship without using the phase comparator circuit. Implementation of this equation requires, that the microprocessor 24 be capable of sampling the instantaneous V output and I output signals at high rates in the range of 8 to 16 million times per second. The instantaneous leakage changes are measured as the differences 22 between the active and return current signals 18 and 20. The leakage changes are instantaneously examined in the feedback loop 26 and if greater than a maximum for leakage while the mode selected is coagulation, then the pulse width of the radio frequency drive, which is part of the electrosurgical unit 13, is reduced to maintain voltage wave-form peaks at a predetermined value while the RMS voltage is reduced to lower the leakage to a maximum allowed level. Feedback loop 26 is in the preferred embodiment an algorithm which would be executed by the microprocessor 24. In FIG. 1 for illustrative purposes, it is drawn as if the feedback loop function was to be accomplished with hardware (components) rather than by software algorithms.

The leakage changes are measured instantaneously as the differences 22 between the active and return current signals 18 and 20 and are examined in the feedback loop 26 and if greater than a maximum for leakage while the mode selected is coagulation then, the frequency at which the leakage current is calculated in the feedback loop 26 is maintained at a maximum allowed level until the phase angle $\theta$ is smaller than the threshold. The leakage changes are measured instantaneously as the differences 22 between the active and return current signals 18 and 20 and are examined in the feedback loop 26 and if greater than a maximum for leakage while the mode selected is cut or bipolar, then the $V_{rms}$ is reduced by lowering the electrosurgical unit 13 radio frequency stage voltage until the differences 22 measured instantaneously indicate that the leakage has been lowered to a maximum allowed level. Phase detection is not the only way to find leakage. Another way is to simply read the signals at 22, and when greater than some predetermined level, then the leakage condition exists. In either case, the leakage sampling rate will be increased as stated.

In another approach for leakage control on an instantaneous basis, the instantaneous leakage changes are measured as the differences 22 between the active and return current signals 18 and 20 and are examined in the feedback loop 26 and if greater than a maximum for leakage while the mode selected is cut or bipolar, then the frequency at which the leakage current is calculated in the feedback loop 26 is changed so the maximum allowed level remains high until the phase angle $\theta$ is smaller than the threshold.

Figure 2:
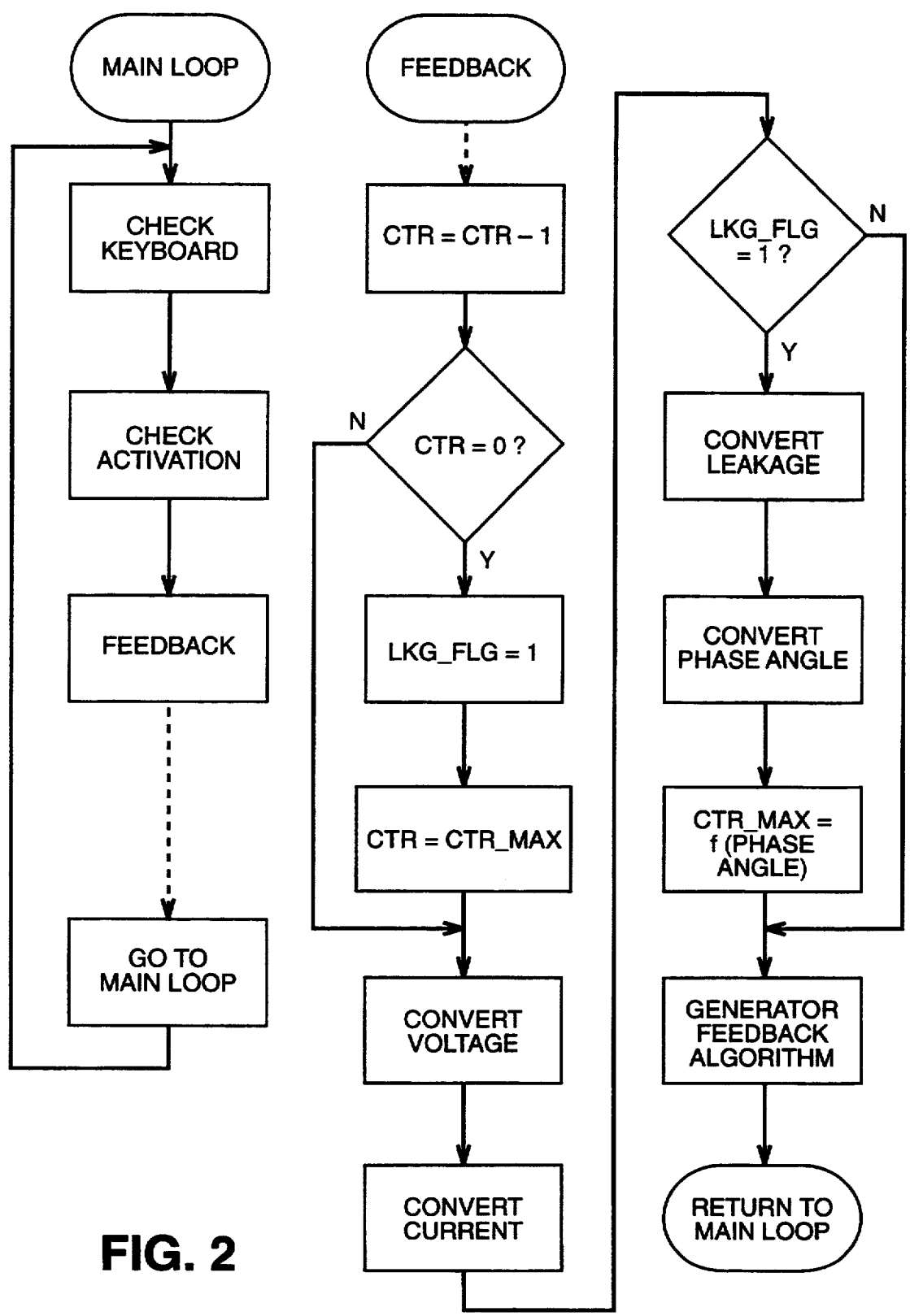
FIG. 2 is a flow diagram with blocks to show the method of performing leakage control on a basis relative to the phase between the voltage and current at a rate sufficient to accommodate transients and variations in load.

In FIG. 2 a block diagram of a method for controlling leakage in a radio frequency electrosurgical unit 13 during its operation under varying tissue loads or through at least transient or open circuit conditions during the initiation or termination of an electrosurgical effect. The active electrode 11 either in or out of electrical contact with the patient's tissue transmits energy to a tip 12 thereof and the method includes the step of providing the electrosurgical unit 13 "ESU" for supplying radio frequency electrosurgical energy at the active output of the ESU. The added step of controlling the flow of the energy through the active output 14 with the electrosurgical unit follows. Then the step of having the return input 15 connected to the electrosurgical unit 13 is used. Thereafter the steps of connecting the electrode 11 to the active output 14 and transmitting electrosurgical radio frequency energy to a patient in an electrosurgical procedure such as cutting, coagulating or a blending thereof is employed. The further steps of connecting the return electrode 16 to the patient and receiving radio frequency energy supplied to the patient during the electrosurgical procedure are selected. The additional step of returning all but a preset maximum amount of radio frequency energy supplied to the return input 15 of the electrosurgical unit 13 is effected. Then the steps of providing the inductive transformer 17 responsive to the active output 14 for supplying the signal 18 of active energy flow and providing the inductive transformer 19 responsive to the return input 15 for supplying the signal 20 of return energy flow are accomplished. Next is the step of using the comparison circuit 21 connected to receive the active and return signals 18 and 20 to measure leakage and determine instantaneous leakage differences 22 at a rate of at least two thousand times per second of the active and return signals 18 and 20. Then, the step of examining the instantaneous differences 22 at a frequency increased in accord with the phase shift 23 between the output signals of proportional voltage 25 and proportional current 18 is performed.

The method has the added step of including the microprocessor 24 and loop 26 having software programmed with one or more algorithms for examining the differences 22 between the active and return current signals 18 and 20 at a frequency dependent on the phase shift 23 found from the output energy supplied by the electrosurgical unit 13. An additional step includes monitoring and controlling the output RMS voltage by reducing the peak voltage of the output wave shaped therefrom or by increasing the crest factor with the closed loop feedback 26.

The added method step of increasing the crest factor by pulse width modulation of the radio frequency drive is used. The added step of having the algorithms for calculating instantaneously the leakage differences 22 between the active and return current signals 18 and 20 and for examining those differences 22 to ascertain the phase shift 23 between the radio frequency voltage and current at the maximums thereof respectively is achieved. The added step of using that particular algorithm for calculating the Cosine of the phase angle $\theta$ is $((V_{max})^2 + (I_{max})^2 - (V\text{-}I)_{max}^2)$ divided by 2 $V_{max} I_{max}$ is included. The added step of comparing the phase angle $\theta$ to a threshold and if it is greater then the frequency at which the differences 22 between the active and return current signals 18 and 20 are examined is increased accordingly.

The added step of examining the differences 22 between the active and return current signals 18 and 20 in the feedback loop 26 and if greater than the preset maximum for radio frequency energy supplied to the return input 15 or for leakage while the mode selected is coagulation, then reducing the pulse width of the radio frequency drive to maintain voltage wave form peaks at a predetermined value as the RMS voltage is reduced to lower the leakage to the maximum allowed level is realized.

The additional or alternate step of examining the differences 22 between the active and return current signals 18 and 20 in the feedback loop 26 and if greater than the preset maximum amount for leakage while the mode selected is coagulation then the frequency at which the leakage current is calculated in the feedback loop 26 so a maximum allowed level is maintained until the phase angle $\theta$ is smaller than the threshold results. The added step of examining the differences 22 between the active and return current signals 18 and 20 in the feedback loop 26 and if greater than the preset maximum for leakage while the mode selected is cut or bipolar then reducing the $V_{rms}$ by lowering the electrosurgical unit 13 radio frequency stage voltage until the differences 22 produce the leakage lowered to the maximum allowed level is a further method step.

The added step of examining the differences 22 between the active and return current signals 18 and 20 in the feedback loop 26 and if greater than the preset maximum for leakage while the mode selected is cut or bipolar then maintaining the frequency at which the leakage current is calculated in the feedback loop 26 so the preset maximum for leakage until the phase angle $\theta$ is smaller than the threshold may offer an extra approach.

The added step of increasing the crest factor by reducing the duty cycle or the pulse width of the output wave shape is then possible.

The flow chart is meant to show the following:

In a microprocessor the main control loop (MAIN LOOP) is running on a continuous basis. The software structure polls through a series of subroutines which monitor key inputs and controls key outputs of the generator.

The example shown shows a simplistic representation of such a control loop. The main loop has associated with it an algorithm which monitors the keyboard and adjusts key pointers and values as a function of keyboard key closures. The main loop also has associated with it an algorithm which monitors the activation inputs from the user. If the generator is activated, key pointers and values are set accordingly.

The main loop also has an algorithm associated with it which is called feedback. This algorithm is active when the generator is activated. The algorithm checks a key operating flag of the software to determine whether the generator is keyed or not. If the generator is not keyed the subroutine is exited. If it is keyed then the feedback algorithm is run.

A counter is associated with the feedback subroutine which sets the bandwidth at which the leakage current is monitored. This counter is decremented each pass through the feedback routine. When the counter equals zero the counter is reset to a calculated maximum value and an internal flag (LKG-FLG) is set to indicate that during this pass through the feedback algorithm the leakage current levels should be checked.

The feedback algorithm then digitizes the output voltage input, digitizes the output current input, and digitizes the leakage current input and the phase angle input. An algorithm is run which recalculates the leakage counter value as a function of the phase angle. As the phase angle increases the frequency at which the leakage current is looked at is increased (i.e., the counter maximum value (CTR-MAX) is decreased).

The control feedback algorithm is then run taking into account the latest values for the output voltage, output current, and leakage current. If the analog to digital conversion is a control bandwidth limiting factor for the design then the feedback bandwidth control of this scheme which changes the bandwidth of the feedback algorithm as a function of the phase angle (which indicates leakage current is increasing) will maximize the feedback bandwidth of a software based control algorithm.

What is claimed is:

1. An apparatus for controlling leakage in a radio frequency electrosurgical system including changes in the load as a function of tissue being electrosurgically treated or transient conditions such as the initiation or termination of an electrosurgical effect wherein an active electrode not in electrical contact with the patient's tissue transmits energy from an electrosurgical unit to a tip of the active electrode comprising:

an electrosurgical unit for providing radio frequency energy at an active output thereof and for controlling the flow of the energy through the active output, the electrosurgical unit having a return input;

an electrode connected to the active output for transmitting electrosurgical radio frequency energy to a patient in an electrosurgical procedure such as cutting, coagulating or a blending thereof;

a return electrode adapted to be connected to the patient for receiving radio frequency energy supplied to the patient during the electrosurgical procedure and connected to the return input for returning it to the return input of the electrosurgical unit;

an inductive transformer connected to and responsive to the active output for providing a signal of active energy flow;

an inductive transformer connected to and responsive to the return input for providing a signal of return energy flow;

a connection between the inductive transformers and the active output and return input, and a comparison circuit connected to receive the active and return signals as a measure of leakage, the comparison circuit having means for determining instantaneous differences at rates of a speed sufficient to handle transient conditions, the comparison circuit having means for examining the differences at a frequency dependent on the phase shift between the output voltage and current of the electrosurgical unit.

2. The apparatus for controlling leakage of claim 1 wherein the electrosurgical unit includes a microprocessor therein, the microprocessor having software programmed with one or more algorithms, the microprocessor software algorithm or algorithms for determining the differences between the active and return current signals and the microprocessor software algorithm or algorithms for examining the differences between the active and return current signals at a frequency dependent on the phase shift between the proportional output voltage and proportional current of the electrosurgical unit.

3. The apparatus for controlling leakage of claim 2 wherein the algorithm for determining the differences between the active and return current signals and for examining the differences ascertains the phase shift between the radio frequency voltage and current at the peaks thereof respectively.

4. The apparatus for controlling leakage of claim 3 wherein the algorithm is the Cosine of the phase angle $\theta$ is $((V_{max})^2 + (I_{max})^2 - (V\text{-}I)_{max}^2)$ divided by $2(V_{max} * I_{max})$.

5. The apparatus for controlling leakage of claim 4 wherein the phase angle $\theta$ is compared in the microprocessor to a threshold and if greater then the frequency at which the differences between the active and return current signals are examined is increased accordingly.

6. The apparatus for controlling leakage of claim 4 wherein the differences between the active and return current signals are examined in the feedback loop of comparison circuit in combination with the microprocessor and if greater than a maximum for leakage while the mode selected is coagulation then the pulse width of the radio frequency drive is reduced to maintain voltage wave-form peaks at a predetermined value while the RMS voltage is reduced to lower the leakage to a maximum allowed level.

7. The apparatus for controlling leakage of claim 4 wherein the differences between the active and return current signals are examined in the feedback loop of the comparison circuit in combination with the microprocessor and if greater than a maximum for leakage while the mode selected is coagulation then the frequency at which the leakage current is calculated is increased in the feedback loop of the comparison circuit so a maximum allowed level is maintained until the phase angle $\theta$ is smaller than the threshold.

8. The apparatus for controlling leakage of claim 4 wherein the differences between the active and return current signals are examined in the feedback loop of the comparison circuit in combination with the microprocessor and if greater than a maximum for leakage while the mode selected is cut or bipolar then the $V_{rms}$ is reduced by lowering the electrosurgical unit radio frequency stage voltage until the differences lower the leakage to a maximum allowed level.

9. The apparatus for controlling leakage of claim 4 wherein the differences between the active and return current signals are examined in the feedback loop of the comparison circuit in combination with the microprocessor and if greater than a maximum for leakage while the mode selected is cut or bipolar then the frequency at which the leakage current is calculated is increased in the feedback loop so the maximum allowed level remains high until the phase angle $\theta$ is smaller than the threshold.

10. The apparatus for controlling leakage of claim 1 wherein the comparison circuit in combination with the microprocessor provides a closed loop feedback for monitoring and controlling the output RMS voltage by reducing the voltage of the output wave shaped therefrom or by increasing the crest factor, which is $V_{rms}$ divided by peak voltage.

11. The apparatus for controlling leakage of claim 10 wherein in the electrosurgical unit, the microprocessor software algorithm or algorithms the crest factor is increased by pulse width modulation of the radio frequency drive.

12. The apparatus for controlling leakage claim 10 wherein the crest factor is increased by the microprocessor reducing the duty cycle or the pulse width of the output wave shape.

13. The apparatus for controlling leakage of claim 1 wherein the microprocessor analyzes the output of the comparison circuit to find the difference, $I_{lkg}$ and if its is about 150 ma then the rate of monitoring is increased.

14. A method for controlling leakage in a radio frequency electrosurgical system during operation under varying tissue loads or through at least transient or open circuit conditions during the initiation or termination of an electrosurgical effect wherein an active electrode in or not in electrical contact with the patient's tissue transmits energy to a tip thereof, having the following steps:

providing an electrosurgical unit having radio frequency energy at an active output thereof;

controlling the flow of the energy through the active output with the electrosurgical unit;

having a return input connected to the electrosurgical unit;

connecting an active electrode to the active output and transmitting electrosurgical radio frequency energy to a patient in an electrosurgical procedure such as cutting, coagulating or a blending thereof;

adapting a return electrode for connection to a patient and receiving radio frequency energy supplied to the patient during the electrosurgical procedure;

returning all but a preset maximum amount of radio frequency energy supplied to the return input of the electrosurgical unit;

providing an inductive transformer connected to and responsive to the active output for supplying a signal of active energy flow;

providing an inductive transformer connected to and responsive to the return input for supplying a signal of return energy flow, and using a comparison circuit connected to receive the active and return signals to measure leakage and determine instantaneous differences at a rate of at least two thousand times per second between the active and return signals, and examining the instantaneous differences at a frequency which is increased in accord with the phase shift between the output signals of proportional voltage and proportional current.

15. The method of claim 14 with the added step of including in the electrosurgical unit a microprocessor having software programmed with one or more algorithms, the microprocessor software algorithm or algorithms for calculating the differences between the active and return current signals and the microprocessor software algorithm or algorithms for examining the differences at a frequency dependent on the phase shift between the output energy of the electrosurgical unit.

16. The method of claim 15 with the added step of using the algorithms for calculating the differences between the active and return current signals and for examining the differences to ascertain the phase shift between the radio frequency proportional voltage and proportional current at the maximums thereof respectively.

17. The method of claim 15 with the added step of examining the differences between the active and return current signals in the feedback loop of the comparison circuit and if greater than the preset maximum of radio frequency energy supplied to the return input or leakage while the mode selected is coagulation then reducing the pulse width of the radio frequency drive to maintain voltage wave form peaks at a predetermined value as the RMS voltage is reduced to lower the leakage to the maximum allowed level.

18. The method of claim 15 with the added step of examining the differences between the active and return current signals in the feedback loop of the comparison circuit and if greater than the preset maximum amount of radio frequency energy supplied to the return input or leakage while the mode selected is coagulation then the frequency at which the leakage current is calculated is increased in the comparison circuit so a maximum allowed level is maintained until the phase angle $\theta$ is smaller than the threshold.

19. The method of claim 15 with the added step of examining the differences between the active and return current signals are in the feedback loop of the comparison circuit and if greater than the preset maximum amount of radio frequency energy supplied to the return input or leakage while the mode selected is cut or bipolar then reducing the $V_{rms}$ by lowering the electrosurgical unit radio frequency stage voltage until the differences produce the leakage lowered to the maximum allowed level.

20. The method of claim 15 with the added step of examining the differences between the active and return current signals in the feedback loop of the comparison circuit and if greater than the preset maximum amount of radio frequency energy supplied to the return input or leakage while the mode selected is cut or bipolar then maintaining the frequency at which the leakage current is calculated is increased in the feedback loop of the comparison circuit so the preset maximum amount of radio frequency energy supplied to the return input or leakage or allowed level is high until the phase angle $\theta$ is smaller than the threshold.

21. The method of claim 15 with the added step of increasing the crest factor by reducing the duty cycle or the pulse width of the output wave shape.

22. The method of claim 16 with the added step of using the particular algorithm for calculating the Cosine of the phase angle $\theta$ is $((V_{max})^2+(I_{max})^2-(V-I)_{max}^2)$ divided by $2 V_{max} I_{max}$.

23. The method of claim 22 with the added step of comparing the phase angle $\theta$ to a threshold and if it is greater than the frequency at which the differences between the active and return current signals are examined is the frequency is increased accordingly.

24. The method of claim 14 with the added step of providing with the comparison circuit in combination with the microprocessor a closed loop feedback for monitoring and controlling the output RMS voltage by reducing the peak voltage of the output wave shaped therefrom or by increasing the crest factor.

25. The method of claim 24 with the added step of increasing by the electrosurgical unit, the microprocessor software algorithm or algorithms the crest factor by pulse width modulation of the radio frequency drive.

* * * * *